(12) United States Patent
Kreber et al.

(10) Patent No.: US 9,775,938 B2
(45) Date of Patent: Oct. 3, 2017

(54) DEVICE FOR CONVEYING A FLUID TO A FILTER UNIT OF A MEDICAL TREATMENT APPARATUS AND METHOD FOR MEASURING THE PRESSURE IN THE FLUID SYSTEM OF SUCH AN APPARATUS

(75) Inventors: Stefan Kreber, Saarbruecken (DE);
Manfred Weis, St. Wendel (DE);
Christoph Wiktor, Gelnhausen (DE);
Arne Peters, Bad Homburg (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 912 days.

(21) Appl. No.: 13/446,231

(22) Filed: Apr. 13, 2012

(65) Prior Publication Data

US 2012/0261316 A1  Oct. 18, 2012

Related U.S. Application Data

(60) Provisional application No. 61/474,774, filed on Apr. 13, 2011.

(30) Foreign Application Priority Data

Apr. 13, 2011  (DE) .......................... 10 2011 016 870

(51) Int. Cl.
*A61M 1/16*  (2006.01)

(52) U.S. Cl.
CPC ........ *A61M 1/1694* (2013.01); *A61M 1/1635* (2014.02); *A61M 2205/3331* (2013.01); *Y10T 137/0318* (2015.04); *Y10T 137/85978* (2015.04)

(58) Field of Classification Search
None
See application file for complete search history.

(56) References Cited

U.S. PATENT DOCUMENTS

| | | |
|---|---|---|
| 4,267,040 A | 5/1981 | Schael |
| 4,530,759 A | 7/1985 | Schael |
| 4,770,769 A | 9/1988 | Schael |
| 2008/0149551 A1 | 6/2008 | Brugger et al. |
| 2009/0124963 A1* | 5/2009 | Hogard ................... A61M 1/16 604/30 |

FOREIGN PATENT DOCUMENTS

| | | |
|---|---|---|
| EP | 2 174 677 A1 | 4/2010 |
| GB | 1 502 859 A | 3/1978 |
| GB | 2 032 136 A | 4/1980 |

OTHER PUBLICATIONS

PCT International Search Report and Written Opinion from PCT/EP2012/001595 mailed on Jul. 13, 2012.
International Preliminary Report on Patentability (IPRP) dated Oct. 15, 2013 in PCT/EP2012/001595.

* cited by examiner

*Primary Examiner* — Chester Barry
(74) *Attorney, Agent, or Firm* — Kilyk & Bowersox, P.L.L.C.

(57) ABSTRACT

A device for conveying a fluid to a filter unit of a medical treatment apparatus, in particular for conveying a dialyzing fluid to a filter unit, in particular a blood treatment unit of an extracorporeal blood treatment apparatus. The device includes one or more devices for measuring pressure in the fluid system. Moreover, a method for measuring the pressure in the fluid system of such a supply device.

15 Claims, 7 Drawing Sheets

DEVICE FOR CONVEYING A FLUID TO A FILTER UNIT OF A MEDICAL TREATMENT APPARATUS AND METHOD FOR MEASURING THE PRESSURE IN THE FLUID SYSTEM OF SUCH AN APPARATUS

CROSS-REFERENCE TO RELATED APPLICATIONS

The present application claims priority to, and the benefit of, U.S. Provisional Application 61/474,774 filed on Apr. 13, 2011. The contents of this provisional application is incorporated herein by reference in its entirety. The present application also claims priority to, and the benefit of, German Patent Application DE 10 2011 016 870.2 filed on Apr. 13, 2011. The contents of this foreign application is incorporated herein by reference in its entirety.

FIELD OF THE INVENTION

The invention relates to a device for conveying a fluid to a filter unit of a medical treatment apparatus, in particular for conveying dialysing fluid to a filter unit, in particular a blood treatment unit of an extracorporeal blood treatment apparatus. Moreover, the invention relates to a method for measuring the pressure in the fluid system of a device for conveying a fluid to a filter unit of a medical treatment apparatus, in particular for conveying fluid to a blood treatment unit of an extracorporeal blood treatment apparatus.

BACKGROUND OF THE INVENTION

Various kinds of treatment apparatuses are known that comprise a treatment unit to be supplied with a fluid. The known treatment apparatuses include, for example, blood treatment apparatuses. During the blood treatment, the patient's blood flows in an extracorporeal blood circuit through the blood treatment unit. In the case of apparatuses for haemodialysis, haemofiltration and haemodiafiltration, the blood treatment unit is a dialyser or filter, which is divided by a semi-permeable membrane into a blood chamber and a dialysing fluid chamber. During the dialysis treatment, the blood flows in an extracorporeal blood circuit through the blood chamber, whilst the dialysing fluid flows in a dialysing fluid circuit through the dialysing fluid chamber of the dialyser.

Considering the large exchange quantities, there is a need with the known methods and apparatuses for blood treatment for exact balancing of the fluid removed from the patient and the fluid fed to the patient during the overall treatment time. Gravimetric and volumetric balancing devices are known.

In order to be able to ensure a continuous flow of dialysing fluid through the dialysing fluid chamber of the dialyser, two balancing chambers are in practice connected in parallel, which supply the dialyser alternately with fresh dialysing fluid. A balancing unit with two balancing chambers is described in for example DE 28 38 414.

Because of the large fluid requirement in dialysis, the preparation of the dialysate from concentrates and pure water (RO water) in the machine has evolved, in order to avoid the storage of fairly large quantities of solutions. The RO water is made available centrally in the clinic and distributed via lines to the dialysis machines in the dialysis stations. In the treatment of an acute renal insufficiency, such as can occur for example after accidents, which calls for intensive-care support for the patient, an RO water connection is generally not present. The dialysing fluid is then made available to the machine by means of containers, for example canisters or bags.

Apparatuses for extracorporeal blood treatment are known, wherein the balancing unit for balancing fresh dialysing fluid against used dialysing fluid is a component part of an article (disposable) intended for one-off use, which is inserted into a suitable receiving unit of the blood treatment apparatus. Balancing units constituted as a disposable are described in for example DE 198 30 928 C1 and DE 195 46 028 C2. In order to balance fresh dialysing fluid against used dialysing fluid, the known disposables comprise chambers which are filled with fresh used dialysing fluid.

For the control of the extracorporeal blood treatment apparatus, it is necessary to measure the pressure at various points of the fluid system. The pressure measurement should take place with a non-invasive procedure, in order to reduce the risk of contamination of the fluid system.

Devices for measuring the pressure in fluid systems are known in extracorporeal blood treatment apparatuses. Pressure measuring devices are known that comprise a pressure sensor which is disposed not in, but rather outside the fluid system. The pressure sensor of the known pressure measuring devices is disposed in a pressure measuring line leading away from the fluid system, behind a hydrophobic sterile filter located in the line that is permeable to air, but impermeable to liquid. The pressure sensor consequently measures the pressure in the air column behind the sterile filter.

Especially in the case of balancing devices constituted as a disposable, a pressure measurement taken with additional elements that are disposed outside the disposable proves to be disadvantageous. The drawbacks result not only from the additional components, but also from additional connections that have to be created when the disposable is connected to the blood treatment apparatus. The creation of these connections not only requires additional labor expenditure, but also increases the risk of malfunctions occurring during the blood treatment.

In order to ameliorate these disadvantages relating to pressure measurements the invention described herein simplifies the pressure measurement in the fluid system of a device for conveying a fluid to a filter unit of a medical treatment apparatus, in particular for conveying a fluid to a blood treatment unit of an extracorporeal blood treatment apparatus.

SUMMARY OF THE INVENTION

In one embodiment of the invention there is provided a device for conveying a fluid to a filter unit of a medical treatment apparatus comprises a fluid system and the arrangement of means for pumping fluid. The fluid system comprises an intake for supplying fresh fluid, a drain for discharging used fluid, a drain for fluid that is supplied to the filter unit, and an intake for fluid that is discharged from the filter unit.

The device according to the invention can be a component part of a medical treatment apparatus or can form a separate assembly. The device according to the invention is preferably a component part of a medical treatment apparatus. The device according to the invention for conveying a fluid to a filter unit of the medical treatment apparatus is referred to below as a supply device.

The device according to the invention and the method according to the invention are based on the fact that the supply device comprises an arrangement of means for creating a flow connection between the means for pumping fluid on the one hand and on the other hand the intake for the supply of fresh fluid, the drain for the discharge of used fluid, the drain for fluid that is supplied to the filter unit, or the intake for fluid that is discharged from the filter unit. These means for creating the flow connection permit a pressure measurement at various points of the fluid system. One or more means for measuring the pressure can be provided for the pressure measurement. In principle, it is possible to measure the pressure at various points of the fluid system using only one means for measuring the pressure, if a flow connection is created in turn between the means for pumping fluid on the one hand and the intakes and drains on the other hand. It is however also possible to measure the pressure at various points of the fluid system simultaneously using a plurality of means for measuring the pressure.

In principle it is not important for the device according to the invention and the method according to the invention how the means for pumping fluid are constituted. The advantages of the device according to the invention and the method according to the invention, however, become particularly noticeable when the means for pumping comprise fluid chambers and means for building up an overpressure and/or underpressure in the chambers, wherein the chambers are a component part of a disposable and the means for building up an overpressure and/or underpressure are disposed on the machine side In a preferred embodiment of the invention, means for pumping fluid are on the one hand a component part of a balancing unit for balancing fresh fluid against used fluid and on the other hand a component part of a recirculation unit for conveying fluid through the filter unit. In a particularly preferred embodiment, the means for pumping comprise four chambers, two of which chambers are respectively a component part of the balancing unit and two chambers a component part of the recirculation unit.

The arrangement of the means for creating a flow connection preferably comprise an arrangement of shut-off elements, in particular valves, which can be operated electromagnetically or pneumatically.

The fluid system preferably comprises an arrangement of lines, which are connected to the intake for supplying fresh fluid, the drain for discharging used fluid, the drain for fluid that is supplied to the filter unit, or the intake for fluid that is discharged from the filter unit. The fluid system preferably also comprises an arrangement of lines which are connected to means for pumping. All the lines are preferably a component part of the disposable.

When the supply device according to the invention is constituted as a device which comprises both a balancing unit and a recirculation unit, the flow connections required for the pressure measurement are in any case created during the operation of the supply device. Consequently, the pressure measurement can be carried out during the normal operation of the balancing and recirculation unit without further interruption of the treatment.

With the device according to the invention and the method according to the invention, additional sensors for the pressure measurement in the various hydraulic branches on the machine side can be spared. Moreover, additional hoses or hydrophobic sterile filters on the disposable side are not required. The insertion of the disposable into a suitable receiving unit of the treatment apparatus likewise does not require additional lines to be connected. The handling of the disposable is thus simplified.

Moreover, the device according to the invention and the method according to the invention can be used for a pressure measurement with an increased reliability, in that the pressure measurement is carried out with a plurality of pressures sensors at a point of the fluid system. The redundancy is therefore increased. The accuracy can also be improved by the fact that the mean value of the pressures measured with a plurality of pressure sensors at a point of the fluid system is calculated.

An example of embodiment of the invention is explained in greater detail below by reference to the drawings.

DETAILED DESCRIPTION OF THE INVENTION

Figure 1:
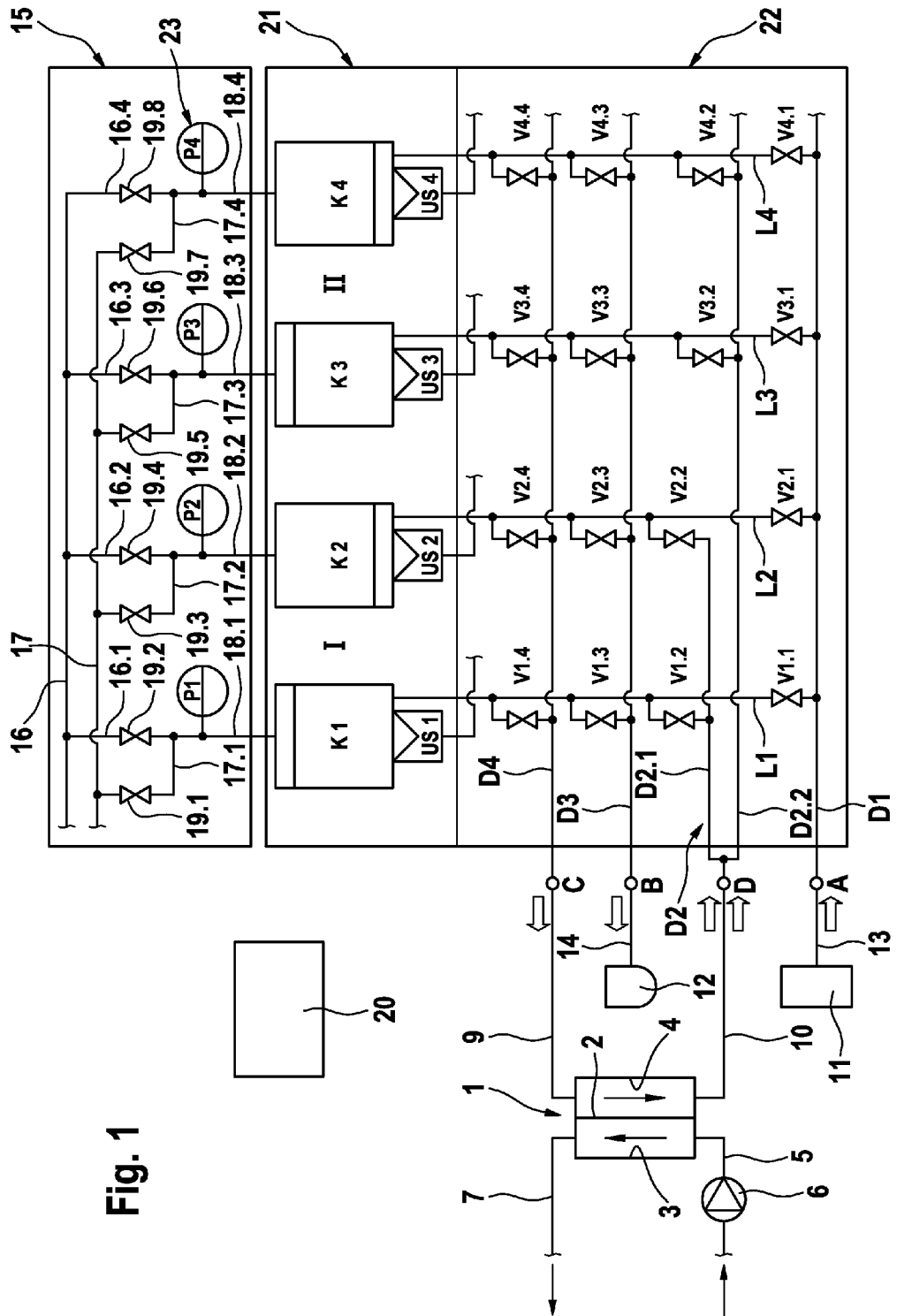
FIG. 1 shows a very simplified schematic representation of a medical treatment apparatus, in particular a dialysis apparatus, which comprises a device for conveying a fluid to a filter unit of the medical treatment apparatus, in particular to the treatment unit of an extracorporeal blood treatment apparatus.

FIG. 1 shows a very simplified representation of the device according to the invention for conveying a fluid to a filter unit of a medical treatment apparatus. In the present example of embodiment, the device according to the invention is used to supply an extracorporeal blood treatment apparatus, in particular a dialysis apparatus, with fresh dialysing fluid, which is made available in a dialysing fluid source, in particular a bag. The device for conveying dialysing fluid is referred to below as a supply device.

The supply device can form an independent unit or be a component part of the dialysis apparatus. The device according to the invention is preferably a component part of the dialysis apparatus. The medical treatment apparatus, in particular the dialysis apparatus, is therefore described below together with the device for conveying a fluid, in particular dialysing fluid, to the filter unit, in particular the dialyser, of the extracorporeal blood treatment apparatus.

The medical treatment apparatus, in particular the dialysis apparatus, comprises a dialyser 1 as a filter unit, which is divided by a semipermeable membrane 2 into a blood chamber 3 and a dialysing fluid chamber 4. Connected to the inlet of blood chamber 3 of dialyser 1 is a blood supply line 5, into which a blood pump 6 is incorporated. Leading away from the outlet of blood chamber 3 of dialyser 1 is a blood discharge line 7, which leads to the patient. A dialysing fluid supply line 9 leads to the inlet of dialysing fluid chamber 4 and a dialysing fluid discharge line 10 leads away from the outlet of dialysing fluid chamber 4. Fresh dialysing fluid is supplied to the dialyser via the dialysing fluid supply line, while used to dialysing fluid is carried away via dialysing fluid discharge line 10.

Fresh dialysing fluid is made available in a dialysing fluid source 11, in particular a bag or a canister. Used dialysing fluid is discharged into a drain 12, which can also be a bag or canister. Dialysing fluid bag 11 is connected via a supply line 13 for fresh dialysing fluid to an intake A of the supply device. Drain 12 is connected via a drain-off line 14 for used dialysing fluid to a drain B of the supply device. Dialysing fluid supply line 9 is connected to a drain C and dialysing fluid discharge line 10 is connected to an intake D of the supply device. Consequently, fresh dialysing fluid is supplied via dialysing fluid supply line 9 of dialysing fluid chamber 4 and used dialysing fluid is discharged via dialysing fluid discharge line 10. Fresh dialysing fluid is thus balanced against used dialysing fluid. In the present example of embodiment, fresh dialysing fluid is fed by means of the supply device to single dialyser 1 of the dialysis apparatus. The dialysis apparatus can however also comprise two filters, as is described for example in DE 10 2009 026 901 A1. Fresh dialysing fluid is then supplied by means of the supply device to the first filter.

The supply device comprises a balancing unit I for balancing fresh dialysing fluid against used dialysing fluid. Moreover, the supply device comprises a recirculation unit II for recirculating dialysing fluid through dialysing fluid chamber 4 of dialyser 1, while fresh dialysing fluid is supplied and used dialysing fluid is discharged.

Balancing unit I comprises a first fluid chamber K1 and a second fluid chamber K2. Recirculation unit II also comprises a first fluid chamber K3 and a second fluid chamber K4. The supply device thus comprises a total of four fluid chambers K1-K4. All the fluid chambers are a component part of an article (disposable) intended for one-off use.

The disposable is inserted into a suitable receiving unit 21 of the dialysis apparatus, which is represented merely by way of indication in FIG. 1.

The supply device comprises, apart from chambers K1-K4, means for routing and means for conveying fresh and used dialysing fluid from dialysing bag 11 to chambers K1 and K2 of balancing unit I and from chambers K1 and K2 of the balancing unit to drain 12 as well as from chambers K3 and K4 of recirculation unit II to dialysing fluid chamber 4 and from dialysing fluid chamber 4 to chambers K3 and K4 of recirculation unit II. These means comprise hose lines or flow paths in a hard part, which are a component part of disposable 21, and a device 15 for subjecting chambers K1-K4 of balancing unit and recirculation unit I and II to an overpressure and/or an underpressure, said device being referred to below as pneumatic device 15. The arrangement of device 15 together with chambers K1-K4 provides for a means for pumping fluid. Thus, the device 15 therein provides a means for building up an overpressure and/or underpressure.

Pneumatic device 15 comprises a pressure line 16, from which spur lines 16.1, 16.2, 16.3, 16.4 branch off, which lead to chambers K1, K2, K3, K4 of balancing unit I and recirculation unit II, in order to build up an overpressure in the individual chambers. Moreover, pneumatic device 15 comprises a pressure line 17, from which spur lines 17.1, 17.2, 17.3, 17.4 branch off, which also lead to chambers K1, K2, K3, K4, in order to build up an underpressure in the individual chambers. The spur lines leading away from first and second pressure line 16, 17 are in each case brought together to a common line segment 18.1, 18.2, 18.3, 18.4 which is connected to chambers K1, K2, K3, K4. An overpressure is present on pressure line 16 and an underpressure is present on pressure line 17. A shut-off element 19.1, 19.2, 19.3, 19.4, 19.5, 19.6, 19.7, 19.8 is incorporated in each case into the individual spur lines. By opening and closing shut-off elements 19.1-19.8, chambers K1-K4 can thus be subjected to overpressure or underpressure, whereby pressure lines 16 and 17, line segments 18.1-18.4, and shut-off elements 19.1-19.8 provide a means for building up an overpressure and/or underpressure in a chamber. The shut-off elements are preferably pneumatically or electromagnetically operated valves. Ventilation valves can also be provided, which however are not represented in FIG. 1.

The control of the shut-off elements takes place with a central control and computing unit 20, which is a component part of the dialysis apparatus. Shut-off elements 19.1-19.8 of pneumatic device 15 are connected by control lines (not represented) to central control and computing unit 20. Control and computing unit 20 (a controlling means) also controls blood pump 6 and all the other units of the dialysis apparatus.

The supply device further comprises an arrangement of lines and shut-off elements which are a component part of disposable 21, in order to connect in each case one of chambers K1-K4 to one of intakes or drains A-D. This arrangement is constituted in the manner of a "matrix", which comprises four "rows" and four "columns".

A line D1, D2, D3, D4 ("rows") is connected to each intake or drain A, B, C, D, while a means for routing fluid such as a line L1, L2, L3, L4 ("columns"), is connected to each chamber K1, K2, K3, K4. Common line segments 18.1-18.4 of pressure lines 16, 17 are connected to one side of the chambers and the connections of fluid lines L1, L2, L3, L4 to the other side of the chambers, so that the connections lie opposite one another. Each line D1-D4, a means for routing fluid, is connected to each line L1-L4 via a shut-off element (valve) V1.1-V 4.4. The shut-off elements are disposed in rows and columns. The arrangement of the valves in the manner of a "matrix" is denoted below as valve arrangement 22, which functions as a means for creating a flow connector. The shut-off elements of valve arrangement 22 are also preferably pneumatically or electromagnetically operated valves.

Furthermore, the supply device comprises means US1, US2, US3, US4 for detecting the filling level of chambers K1, K2, K3, K4, which are represented solely by way of indication. The means for detecting the filling level of the chambers are connected to central control and computing unit 20.

The individual operating steps, in which fluid flows into chambers K1-K4 and out of chambers K1-K4, are described below.

The operating steps of recirculation unit II are first described, with which a flow of dialysing fluid is maintained through dialysing fluid chamber 4 of dialyser 1.

Figure 2A:
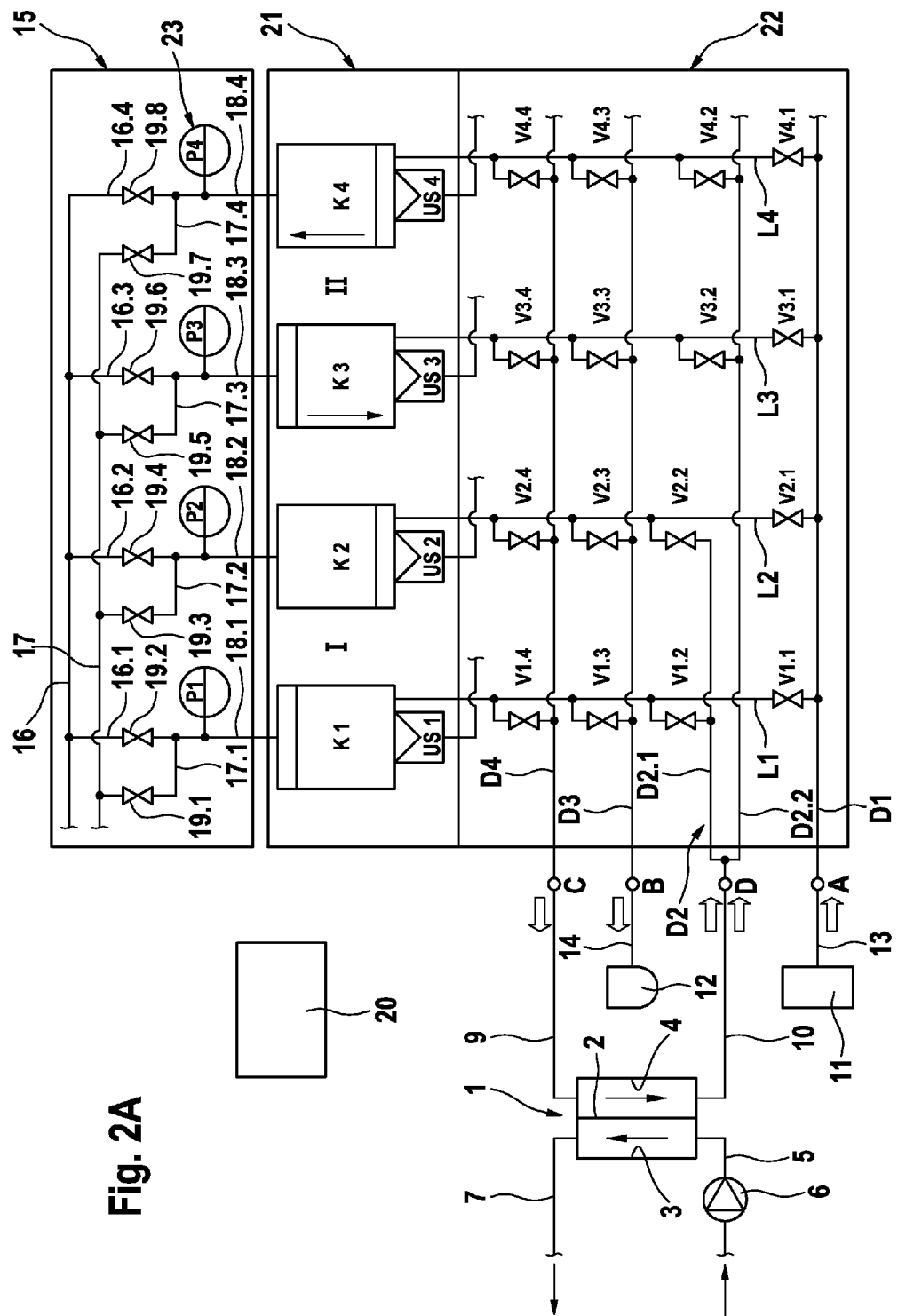
FIGS. 2A and 2B show the individual operating steps of the recirculation unit of the device according to the invention and FIGS. 3A-3D show the individual operating steps of the balancing unit of the device according to the invention.
Figure 2B:
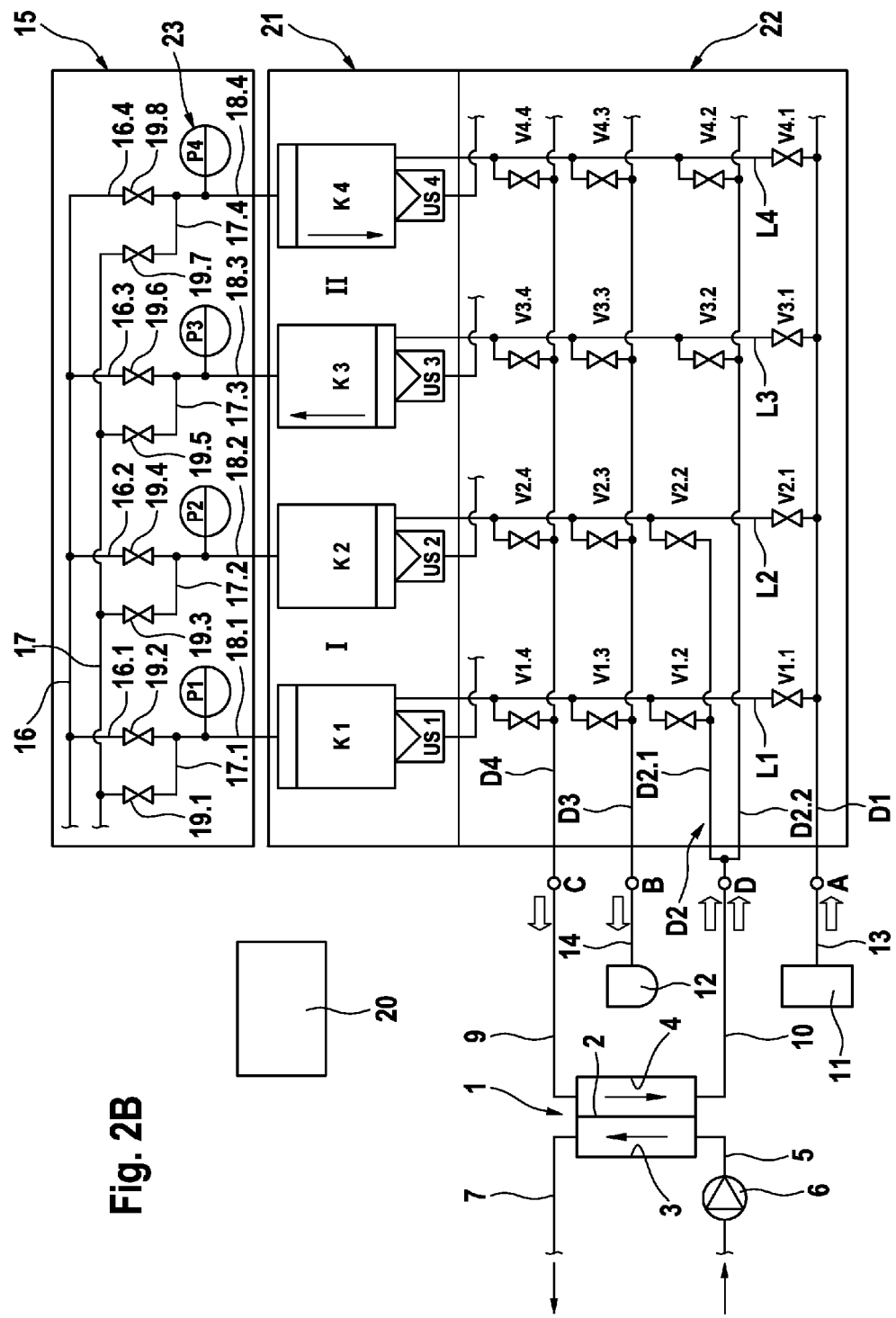

FIGS. 2A and 2B illustrate the successive operating steps of successive operating cycles, in which dialysing fluid flows into and respectively out of chambers K3 and K4 of recirculation unit II. Shut-off elements V1.1-V 4.4, which are opened by control and computing unit 20, are indicated in FIGS. 2A and 2B.

FIG. 2A shows the first operating step of an operating cycle. In the first operating step, fresh dialysing fluid flows out of chamber K3 into dialysing fluid chamber 4, while used dialysing fluid flows out of dialysing fluid chamber 4 of dialyser 1 into chamber K4 of recirculation unit II. For this purpose, control and computing unit 20 opens valves V3.4 and V4.2 of valve arrangement 22 and valves 19.6 and 19.7 of pneumatic device 15, while the other valves are closed. Consequently, chamber K3 is subjected to an overpressure and chamber K4 to an underpressure, so that dialysing fluid flows via lines L3, D4, D2.2, L4 out of chamber K3 through dialysing fluid chamber 4 of dialyser 1 into chamber K4. The flow direction is marked by arrows in FIG. 1A. The fluid flow is reversed in the second operating step of the same operating cycle. The control and computing unit now opens valves V4.4 and V3.2 of valve arrangement 22 and valves 19.8 and 19.5 of pneumatic device 15, so that dialysing fluid flows out of chamber K4 through dialysing fluid chamber 4 into chamber K3 of balancing unit II.

The operating cycle described above is again followed by the same operating cycle with two operating steps.

While dialysing fluid is conveyed continuously with recirculation unit I through dialyser 1, fresh dialysing fluid is balanced against used dialysing fluid with balancing unit I, wherein fresh dialysing fluid is supplied from dialysing fluid source 11 and used dialysing fluid flows away into drain 12. The individual operating steps of this operating cycle are described below by reference to FIGS. 3A-3E. The double arrows in K3 and K4 of FIGS. 3A-3E symbolise the continuous recirculation of dialysing fluid during the balancing process.

Figure 3A:
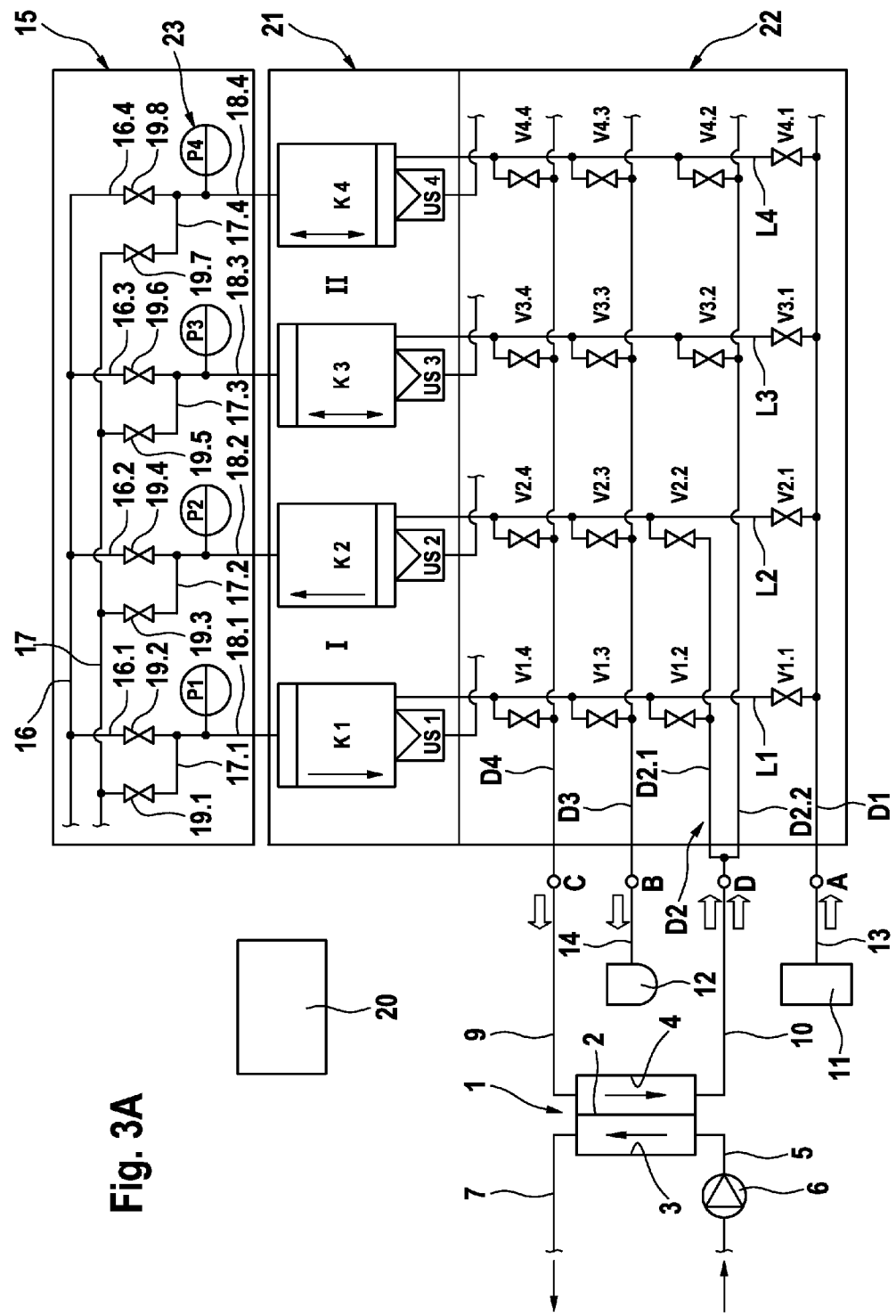

It is assumed that chamber K1 is filled with fresh dialysing fluid and chamber K2 is empty in the first operating step of an operating cycle. In the first operating step, valves V1.4 and V2.2 of valve arrangement 22 and valves 19.2 and 19.3 of pneumatic device 15 are opened by control and computing unit 20, the other valves being closed. Chamber K1 is thus subjected to overpressure and chamber K2 of balancing unit I to underpressure. Fresh dialysing fluid thus flows out of chamber K1 via lines L1, D4, D2.1, L2 through dialysing fluid chamber 4 of dialyser 1 and displaces used dialysing fluid out of dialysing fluid chamber 4 into chamber K2 (FIG. 3A).

Figure 3B:
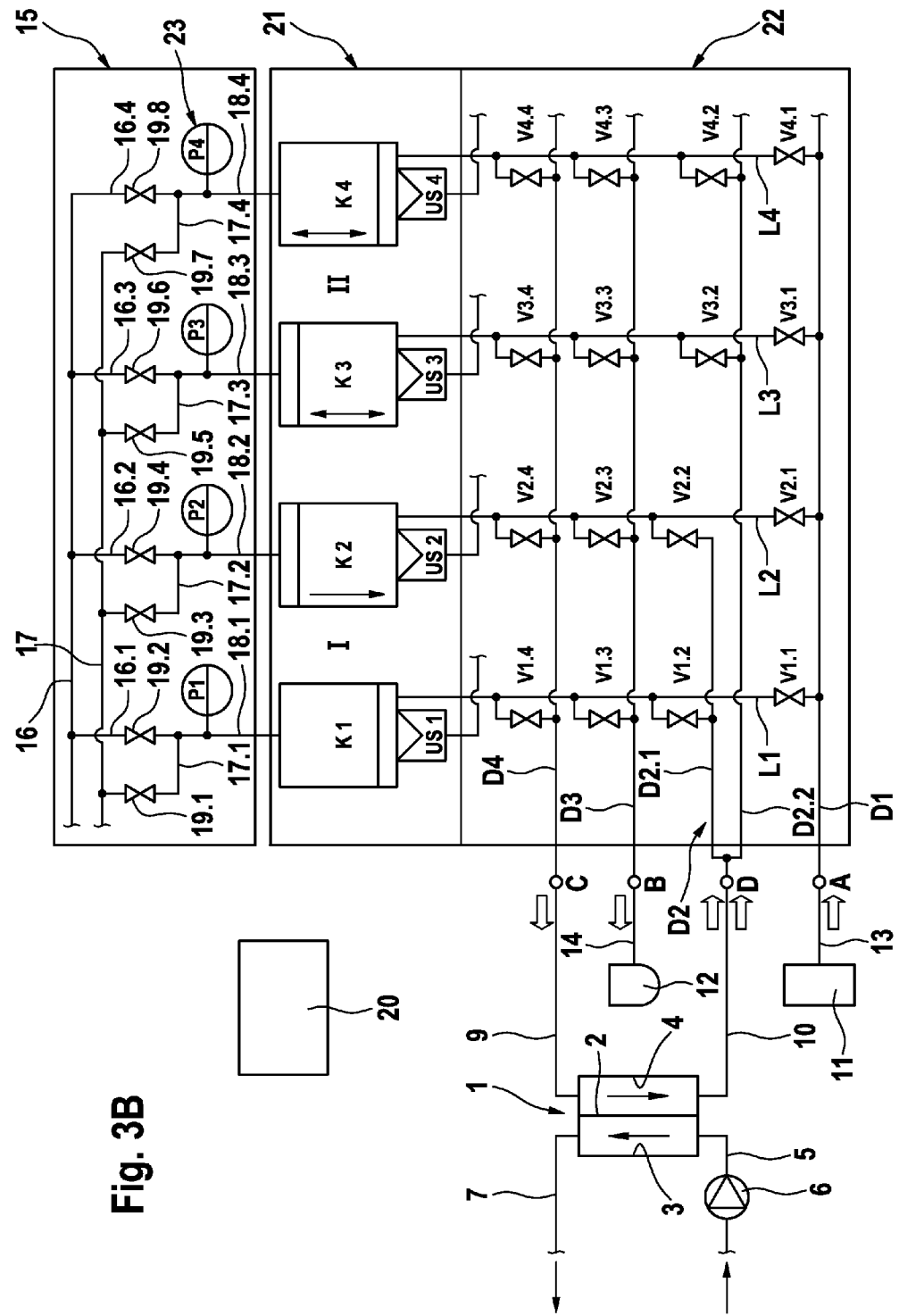

In the second operating step, the used dialysing fluid is discarded from chamber K2. For this purpose, valve V2.3 of valve arrangement 21 and valve 19.4 of pneumatic device 15 are opened, while the other valves are closed. Since chamber K2 is subjected to an overpressure, the used dialysing fluid flows into drain 12 (FIG. 3B).

Figure 3C:
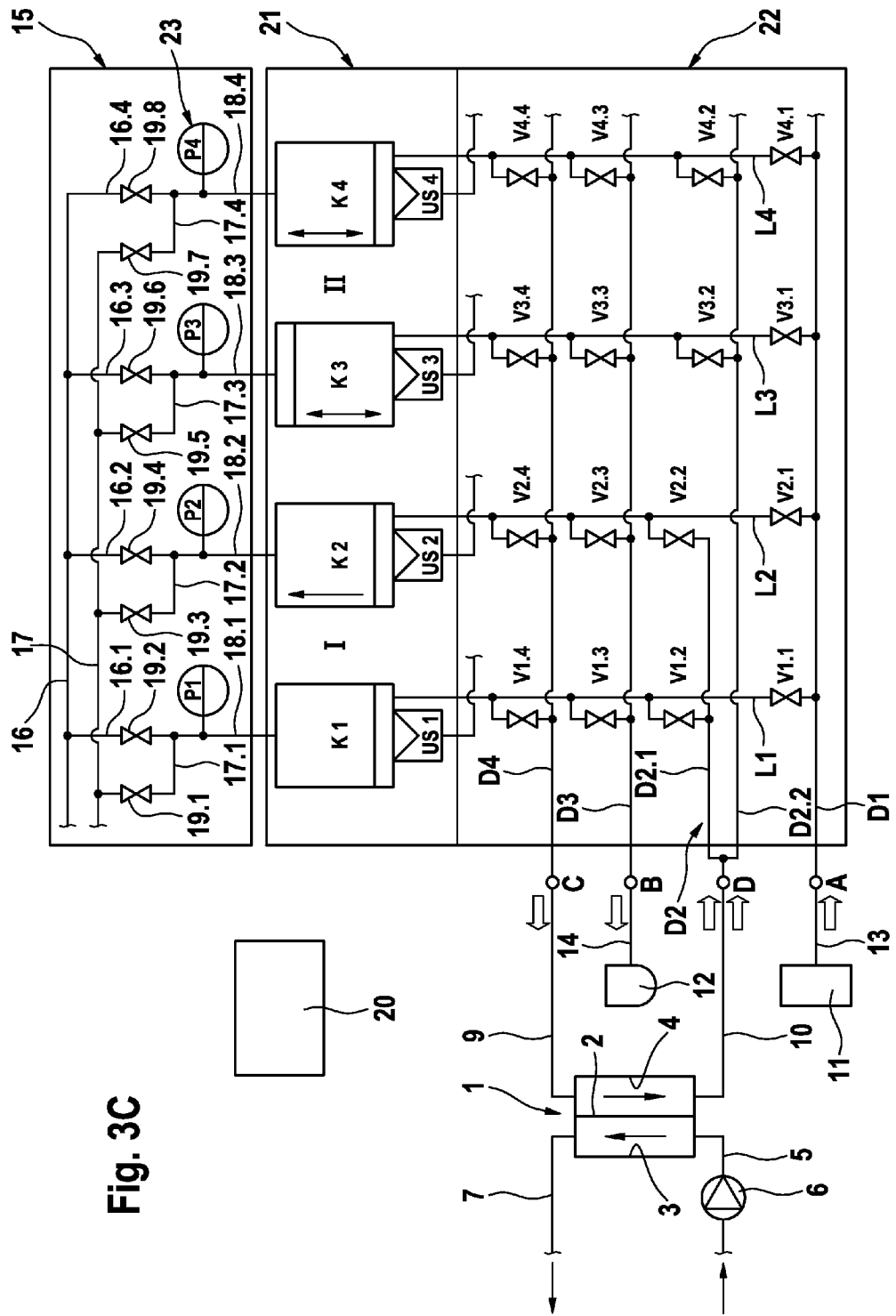
Figure 3D:
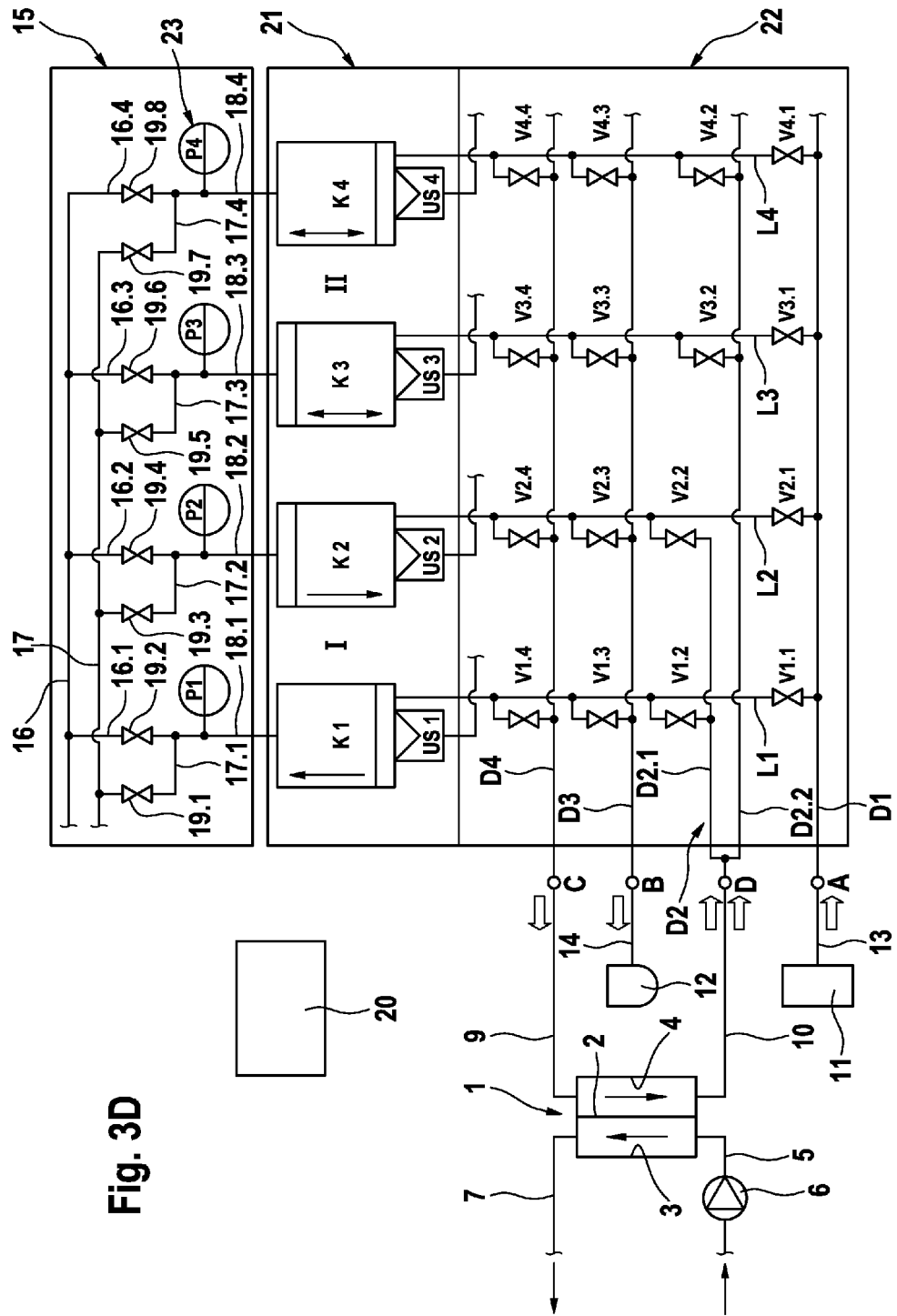

A third operating step follows, in which chamber K2 is filled with fresh dialysing fluid from dialysing fluid source 11. For this purpose, valve V2.1 of valve arrangement 22 and valve 19.3 of pneumatic device 15 are opened, while the other valves are closed, so that fresh dialysing fluid is sucked into chamber K2 (FIG. 3C).

The fourth operating step now follows, in which the fresh dialysing fluid from chamber K2 displaces used dialysing fluid into chamber K1 via dialyser 1. For this purpose, valves V2.4 and V1.2 of valve arrangement 22 and valves 19.4 and 19.1 of pneumatic device 15 are opened, while the other valves are closed, so that an overpressure is built up in chamber K2 and an underpressure in chamber K1. The operating steps described above form an operating cycle, which is followed again by an operating cycle which comprises the operating steps described above (FIG. 3D).

Chambers K1 and K2 of balancing unit I thus remove fresh dialysing fluid from dialysing fluid bag 11 in order to supply the dialysing fluid to the dialysing fluid circuit. Fresh dialysing fluid is thereby balanced against used dialysing fluid, wherein fluid can be withdrawn from (ultrafiltration) or fluid can be supplied to the fluid system. The supply or the withdrawal of fluid can take place by the fact that more or less fluid is supplied to or withdrawn from the one or other chamber. Instead of a differing filling of the chambers with dialysing fluid, it is also possible in one or more operating steps to withdraw only used dialysing fluid from the fluid system or to supply only fresh dialysing fluid to the fluid system, in order to supply fluid to the system or to withdraw it therefrom Control and computing unit 20 controls the switch-over of individual valves V1.1. to V4.1 depending on the filling level of the chambers. Since the chambers and the associated lines can have differing volumes, it is not ensured solely by detecting the filling level that equal quantities of fresh dialysing fluid are balanced against used dialysing fluid. This possible error is avoided by the fact that both chambers are each filled with fresh and with used dialysing fluid and are cyclically interchanged. Possible errors are thus compensated for over the individual operating cycles.

In the present example of an embodiment, the individual chambers can be subjected both to an overpressure and to an underpressure in order to convey dialysing fluid from the one into the other chamber. In principle, however, it is also possible to subject only the one or the other of the two chambers to an overpressure or underpressure.

Since the balancing unit comprises only two chambers, individual operating steps in which dialysing fluid does not flow through the dialyser arise with the alternating filling of the chambers with fresh and used dialysing fluid. Consequently, the fluid flow through the dialyser is discontinuous. However, this is not disadvantageous, since the fluid flow through the recirculation unit is in any case maintained. Moreover, it is possible with the recirculation unit to set higher flow rates than the flow rate at which fresh dialysing fluid is supplied or used dialysing fluid discharged. A relatively small consumption of dialysing fluid thus results even with a high flow rate through the dialyser. This is advantageous especially in the case of dialysis apparatuses for acute dialysis.

The operation of balancing unit I and of recirculation unit II permits the simple measurement of the pressure both in lines L, D of the fluid system of the supply device as well as in lines 9, 10, 13, 14 of the fluid system of the extracorporeal blood treatment apparatus, which are connected to lines L, D of the fluid system of the supply device.

In order to measure the pressure, the supply device comprises a pressure measuring device 23, which comprises means for measuring the pressure. The means for measuring the pressure are pressure sensors P1, P2, P3, P4, which are connected to common line segments 18.1, 18.2, 18.3, 18.4 of pressure lines 16, 17, so that the pressure sensors detect the pressure in individual chambers K1, K2, K3, K4. In the present example of embodiment, pressure sensors P1-P4 are not a component part of the disposable, but are disposed on the machine side. Pressure measuring device 23 is connected via a data line (not shown) to central computing and control unit 20 of the blood treatment apparatus. The pressure measurement values for the control of the blood treatment are evaluated in the central computing and control unit.

During the operation of balancing unit and recirculation unit I, II described by reference to FIGS. 2 and 3, shut-off elements V1.1-V4.4 are opened or closed, so that fresh dialysing fluid is balanced against used dialysing fluid and dialysing fluid flows through balancing chamber 2 of dialyser 1. When individual shut-off elements are opened, a flow connection is produced between lines L1, L2, L3, L4 and lines D1, D2, D3, D4. Consequently, the pressure in lines D1, D2, D3, D4 can be measured with the respective pressure sensor P1, P2, P3, P4 that detects the pressure in the chamber which is connected to respective line L1, L2, L3, L4. For example, pressure sensor P1 measures the pressure in line D4 and line 9 when shut-off element V1.4 is opened, but all the other shut-off elements are closed. The pressure in all the lines can thus be measured by opening and closing the respective shut-off elements.

In the present example of an embodiment, pressure measuring device 23 comprises four pressure sensors P1-P4. It is thus possible to measure the pressure in a plurality of lines simultaneously. It is however also possible for the pressure measuring device to comprise only one, two or three pressure sensors. Even when the pressure measuring device comprises only one pressure sensor, for example only pressure sensor P1, the pressure in all the lines can be measured with the single pressure sensor. In this case, the pressure measurement in all the lines can however only take place one after the other. Simultaneous measurement of the pressure at four points of the fluid system requires the four pressure sensors P1-P4.

Pressure sensors P1-P4 can measure the pressure in the chambers continuously, the measured values being read out only at specific times. These times points are a result of the step sequence in the operation of the chambers.

Valve arrangement 22 also permits an initial functional test of individual pressure sensors P1-P4, wherein the pressure sensors are connected to one another by opening or closing respective shut-off elements V1.1-V4.4. A functional test of the pressure sensors as well as a calibration of the sensors is thus possible, since the measurement of the pressure with all the sensors must lead to the same measurement result.

The invention claimed is:

1. A medical treatment system comprising a medical treatment apparatus and an insertable device for conveying a fluid to a filter unit of the medical treatment apparatus, wherein: the medical treatment apparatus comprises
    a pneumatic device including a plurality of pressure lines,
    at least one pressure sensor,
    a filter unit,
    a receiving unit configured to receive the insertable device, and
    a fluid system including
        an intake configured to supply fresh fluid,
        a drain configured to discharge used fluid,
        a drain for fluid that is supplied to the filter unit, and
        an intake for fluid that is discharged from the filter unit;
    the insertable device comprises four chambers and four respective fluid lines, each chamber being in fluid communication with a respective one of the four fluid lines, the at least one pressure sensor forming no component part of the insertable device; and
    the medical treatment system further comprises
        a control and computing unit,
        a pumping arrangement configured to pump the fresh and the used fluid, the pumping arrangement comprising control lines connecting the pneumatic device to the control and computing unit, and further comprising the plurality of pressure lines in communication with the four chambers of the insertable device and configured to build up at least one of an overpressure or an underpressure in at least one of the four chambers,
        a fluid communication arrangement comprising an arrangement of shut-off elements and control lines connecting the shut-off elements to the control and computing unit, the fluid communication arrangement being configured to create flow connections between
            (a) the pumping arrangement configured to pump the fresh and the used fluid, and
            (b) the intake configured to supply fresh fluid, the drain configured to discharge used fluid, the drain for fluid that is supplied to the filter unit, and the intake for fluid that is discharged from the filter unit, and
        a pressure measuring arrangement comprising the at least one pressure sensor and data lines connecting the at least one pressure sensor to the control and computing unit, the pressure measuring arrangement being configured to measure the pressure in the fluid system by measuring the pressure within at least one of the four chambers, using the at least one pressure sensor.

2. The medical treatment system according to claim 1, wherein the pumping arrangement configured to pump the fresh and the used fluid is a component part of a balancing unit configured to balance the fresh fluid against the used fluid.

3. The medical treatment system according to claim 1, wherein the pumping arrangement configured to pump the fresh and the used fluid is a component part of a recirculation unit configured to convey fluid through the filter unit.

4. The medical treatment system according to claim 1, wherein two chambers are in each case a component part of a balancing unit configured to balance the fresh fluid against the used fluid and two chambers are a component part of a recirculation unit configured to convey fluid through the filter unit.

5. The medical treatment system according to claim 1, wherein the fluid system further comprises an arrangement of lines that are connected to the intake configured to supply fresh fluid, the drain configured to discharge used fluid, the drain for fluid that is supplied to the filter unit, and the intake for fluid that is discharged from the filter unit.

6. The medical treatment system according to claim 1, wherein the fluid system further comprises an arrangement of lines, which are connected to the pumping arrangement configured to pump.

7. The medical treatment system according to claim 1, wherein the fluid system and the fluid communication arrangement configured to create the flow connections are component parts of the insertable device.

8. The medical treatment system according to claim 1, wherein the fresh and the used fluid is a dialysing fluid.

9. An extracorporeal blood treatment apparatus comprising the medical treatment system according to claim 1.

10. The extracorporeal blood treatment apparatus according to claim 9, wherein the filter unit is a blood treatment unit.

11. The extracorporeal blood treatment apparatus according to claim 10, wherein the blood treatment unit is a dialyser, or a dialysing fluid filter.

12. A method for measuring pressure in the fluid system of the medical treatment system of claim 1, comprising:
    inserting the insertable unit into the receiving unit; and
    measuring the pressure in the fluid system using the at least one pressure sensor of the medical treatment apparatus.

13. The method according to claim 12, wherein the fluid system further comprises: an arrangement of fluid lines that are connected to the intake configured to supply fresh fluid, the drain configured to discharge used fluid, the drain for fluid that is supplied to the filter unit, and the intake for fluid that is discharged from the filter unit; and an arrangement of lines that are connected to the pumping arrangement, wherein pressure in the pumping arrangement is measured in order to measure the pressure in the fluid lines.

14. The method according to claim 12, wherein pressure in the fluid system is measured after opening at least one of the shut-off elements.

15. The method according to claim 12, wherein the fresh fluid is a dialysing fluid.

* * * * *